United States Patent
McCausland et al.

(10) Patent No.: US 7,326,294 B2
(45) Date of Patent: Feb. 5, 2008

(54) PREPARATION OF SMALL CRYSTALS

(75) Inventors: Linda Jane McCausland, Abingdon (GB); David Reay, Brightwell-cum-Sotwell (GB)

(73) Assignee: Accentus PLC, London (GB)

( * ) Notice: Subject to any disclaimer, the term of this patent is extended or adjusted under 35 U.S.C. 154(b) by 308 days.

(21) Appl. No.: 10/513,153

(22) PCT Filed: Apr. 8, 2003

(86) PCT No.: PCT/GB03/01540

§ 371 (c)(1),
(2), (4) Date: Nov. 2, 2004

(87) PCT Pub. No.: WO03/092851

PCT Pub. Date: Nov. 13, 2003

(65) Prior Publication Data

US 2005/0155541 A1 Jul. 21, 2005

(30) Foreign Application Priority Data

May 2, 2002 (GB) ............... PCT/GB2002/002006
Aug. 24, 2002 (GB) ............................. 0219815.8

(51) Int. Cl.
*B01D 9/00* (2006.01)
*C30B 1/00* (2006.01)

(52) U.S. Cl. .............. 117/70; 117/34; 117/35; 117/45; 117/50; 117/68; 117/159; 117/901; 34/312; 34/368; 34/373; 424/489; 239/5; 239/128; 239/130; 239/132

(58) Field of Classification Search ............... 117/68, 117/200, 34, 35, 45, 50, 70, 159, 901; 34/312, 34/368, 373; 424/489; 159/3; 426/388
See application file for complete search history.

(56) References Cited

U.S. PATENT DOCUMENTS 2,396,689 A * 3/1946 Davis .................... 159/4.2
2,970,057 A * 1/1961 Nava et al. .............. 426/388

(Continued)

FOREIGN PATENT DOCUMENTS

DE 10004860 10/2000

(Continued)

OTHER PUBLICATIONS

English language abstract of JP 3199119.

*Primary Examiner*—Yogendra N Gupta
*Assistant Examiner*—Seyed Masoud Malekzadeh
(74) *Attorney, Agent, or Firm*—William H. Holt

(57) ABSTRACT

Small crystals are made by mixing a solution of a desired substance with an anti-solvent in a fluidic vortex mixer in which the residence time is less than 1s, for example 10 ms. The liquid within the fluidic vortex mixer (12) is subjected to high intensity ultrasound from a transducer (20, 22). The solution very rapidly becomes supersaturated, and the ultrasound can induce a very large number of nuclei for crystal growth. Small crystals, for example less than 5 µm, are formed. The resulting suspension is treated so as to add or remove ingredients, and then spray dried using an atomizer tuned to create small droplets in such a way that each droplet should contain not more than one crystal. Crystal agglomeration is hence prevented.

16 Claims, 3 Drawing Sheets

U.S. PATENT DOCUMENTS

| | | | |
|---|---|---|---|
| 4,489,503 A * | 12/1984 | Browne et al. | 34/368 |
| 5,624,530 A * | 4/1997 | Sadykhov et al. | 159/3 |
| 6,308,434 B1 * | 10/2001 | Chickering et al. | 34/373 |
| 6,408,536 B1 * | 6/2002 | Deusser et al. | 34/312 |
| 6,482,438 B1 * | 11/2002 | Singh et al. | 424/489 |
| 6,601,776 B1 * | 8/2003 | Oljaca et al. | 239/5 |
| 6,723,346 B1 * | 4/2004 | Nowotny et al. | 424/489 |
| 2003/0051659 A1 * | 3/2003 | Rauls et al. | 117/68 |
| 2003/0106488 A1 * | 6/2003 | Huang et al. | 117/68 |

FOREIGN PATENT DOCUMENTS

| | | |
|---|---|---|
| EP | 0449454 | 10/1991 |
| EP | 1048668 | 4/2000 |
| EP | 1127963 | 8/2001 |
| GB | 2276567 A * | 10/1994 |
| GB | 2341120 | 3/2000 |
| JP | 3199119 | 8/1991 |
| WO | 96/32149 | 10/1996 |
| WO | 98/47493 | 10/1998 |
| WO | 00/27363 | 5/2000 |
| WO | 00/29545 | 5/2000 |
| WO | 00/38811 | 7/2000 |
| WO | 02/089942 | 11/2002 |

* cited by examiner

PREPARATION OF SMALL CRYSTALS

This invention relates to an apparatus and a process for preparing small crystals of size less than 10 μm.

The control of crystal and precipitate particle size and morphology is very important in some circumstances, in particular in the pharmaceutical and agro-chemical industries in which the final product form is a fine powder. The way in which an active ingredient behaves, whether in the body or upon the surface of a leaf for example, depends critically upon the particle size of the product, and the particular crystal form. Small particles may be made by processes such as milling, but such processes may have a detrimental effect on the material properties and may also produce a significant proportion of particles which are too small for the desired use, so that crystallisation of crystals in the desired size range directly from a solution would be desirable.

For many years it has been known to bring about crystallisation by mixing a solvent containing a product to be crystallised with an anti-solvent, so that after mixing the solution is supersaturated and crystallisation occurs. GB 2 341 120 A describes a system in which the mixing utilizes a fluidic vortex mixer, and in which the emerging mixture is supplied directly to a precipitate entrapment device. The term anti-solvent means a fluid which promotes precipitation from the solvent of the product (or of a precursor for the product). The anti-solvent may comprise a cold gas, or a fluid which promotes the precipitation via a chemical reaction, or which decreases the solubility of the product in the solvent; it may be the same liquid as the solvent but at a different temperature, or it may be a different liquid from the solvent. EP 0 449 454 A (=GB 2 242 376) describes a system for bringing about on-line precipitation in which liquid reagents are thoroughly mixed using a fluidic vortex mixer, the mixture then being passed through a vessel comprising linked vortex cells in which a pulsed flow ensures a well-defined residence time, hence ensuring particles of a selected mean size are created. The benefits of applying intense ultrasound during a crystallisation process have also been recognized, for example as described in an article by Chris Price in Pharmaceutical Technology Europe, October 1997, as such insonation can be used to initiate nucleation, so overcoming the problems that can arise from supersaturation.

WO 02/089942 describes a method of performing crystallisation in which a saturated solution is mixed with an anti-solvent by passage through a fluidic vortex mixer, in which the liquid within the fluidic vortex mixer is subjected to high intensity ultrasound. A fluidic vortex mixer comprises a vortex chamber with two or more peripheral inlets, at least one of which is substantially tangential, and with an axial outlet. Such a device can achieve very rapid and thorough mixing in a very short space of time; for example the residence time in the mixer may be less than 0.5 s, or even less than 0.1 s, for example 20 ms or 10 ms, though usually at least 1 ms. The chamber is substantially cylindrical, and contains no baffles to disrupt the vortex flow. Such a fluidic mixer can therefore achieve a very high degree of supersaturation, because of the rapid and very thorough mixing with the anti-solvent. This process can enable crystals of a material to be formed which are less than 10 μm in size, for example less than 5 μm or less than 1 μm. Such small crystals may be of a suitable size for use in inhalers.

Although such a process enables you to make small crystals of a well-defined size, drying the crystals to remove all the liquid associated with them and so to prepare a free-flowing powder is not straightforward. Agglomeration of the crystals must be prevented. Furthermore the liquid phase may contain other solutes in solution, and the crystals must be separated from these solutes before drying. Conversely, it may be desirable to add other ingredients before drying the crystals. Filtration or centrifuging, followed by oven or drum drying, which is known for use with larger crystals, is inappropriate with such small crystals as the filtration rate would be very slow and the crystals will tend to form a cake or large agglomerates in the dryer. The use of spray drying to dry crystals has been suggested for example in EP 1 048 668 (for riboflavin . . . ), and is also suggested in EP 976 750 (for Z-valacyclovir), but the problem of preventing aggregation or agglomeration has not been considered.

According to the present invention there is provided a method for preparing dry crystals from a suspension of crystals in a liquid, the crystals being of a well-defined size that is in the range 1 μm to 10 μm, the method comprising spray drying the suspension using an atomiser tuned to create small droplets in such a way that each droplet should contain not more than one crystal.

The atomiser may for example be a pneumatic, rotary or ultrasonic/piezoelectric atomiser. If the droplets are sufficiently small and/or the suspension sufficiently dilute, then the small droplets are very unlikely to contain more than one crystal, so that the drying process generates single unagglomerated crystals. Hence the method may comprise treating the suspension so as to add or remove ingredients or dilute the suspension, prior to the spray-drying step. Many of the droplets will in fact contain no crystals at all, and therefore will evaporate completely. Typically the diameter of the droplets might be about two or three times the crystal size. If the droplets are more than about twice the crystal size there is a risk that some droplets may contain more than one crystal, but this risk can be significantly reduced by diluting the suspension before the drying process, for example with antisolvent.

The present invention also provides a method of preparing dry crystals from a saturated solution, in which the saturated solution is mixed with an anti-solvent by passage through a fluidic vortex mixer, the liquid within the fluidic vortex mixer being subjected to high intensity ultrasound to initiate crystallisation and so to form a suspension of crystals of a well-defined size that is in the range 1 μm to 10 μm, treating the suspension so as to add or remove ingredients or dilute the suspension, and then spray drying the suspension using an atomiser tuned to create small droplets in such a way that each droplet should contain not more than one crystal.

Drying in the manner described above overcomes the problem of agglomeration. Hence the resulting crystals will be free-flowing and of a narrow size distribution.

Prior to spray drying it may be desirable to add other ingredients, and these may be crystalline or may be in solution. Hence the method may involve the step of mixing the suspension of crystals with such other ingredients prior to the spray drying. An ingredient added as a solution may then be adsorbed onto the surface of the crystals, so that the resulting dry crystals are coated with that ingredient. As intimated above it may also be desirable to add additional liquid to the suspension to lower the concentration and so reduce the risk of two crystals being present in a droplet.

Such mixing may be carried out in a batch mixing tank, or with a fluidic vortex mixer.

Furthermore, prior to spray drying it may be necessary to remove other solutes from the suspension. This would be particularly the case if the crystals had been generated by reaction crystallisation. Some form of solid-liquid separation and washing is clearly required before spray drying, but the very small crystal size makes separation and washing on a filter or centrifuge extremely slow. Preferably the suspension is passed through a train of two or more hydrocyclones in counter-current to a wash liquid. The wash liquid may be the antisolvent, or another liquid in which the crystals are insoluble. Alternatively the suspension may be diluted with a wash liquid, and then subjected to cross-flow filtration using a microfilter or ultrafilter to remove the excess liquid. If the crystal size is greater than about 2 μm then the use of hydrocyclones is satisfactory, but for crystal sizes less than about 2 μm the use of cross-flow filtration may be necessary as it is difficult to operate a hydrocyclone with a sufficiently small cut-off size.

The invention also provides apparatus for performing the said methods.

The invention will now be further and more particularly described, by way of example only, and with reference to the accompanying drawings, in which:

FIG. 4b shows an alternative to the apparatus of FIG. 4a;

Figure 1:
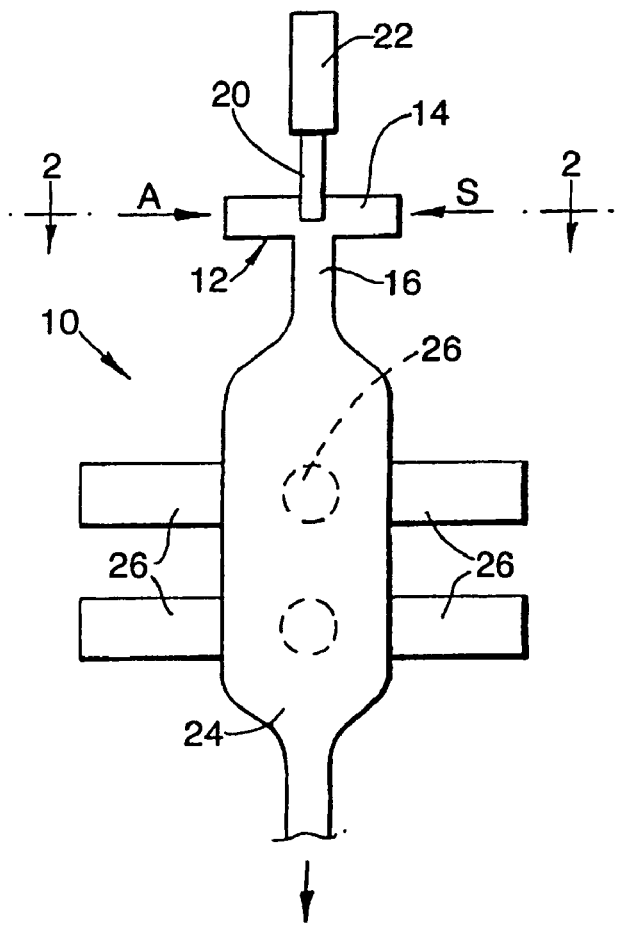
FIG. 1 shows a longitudinal sectional view of a crystallisation apparatus incorporating a fluidic mixer.
Figure 2:
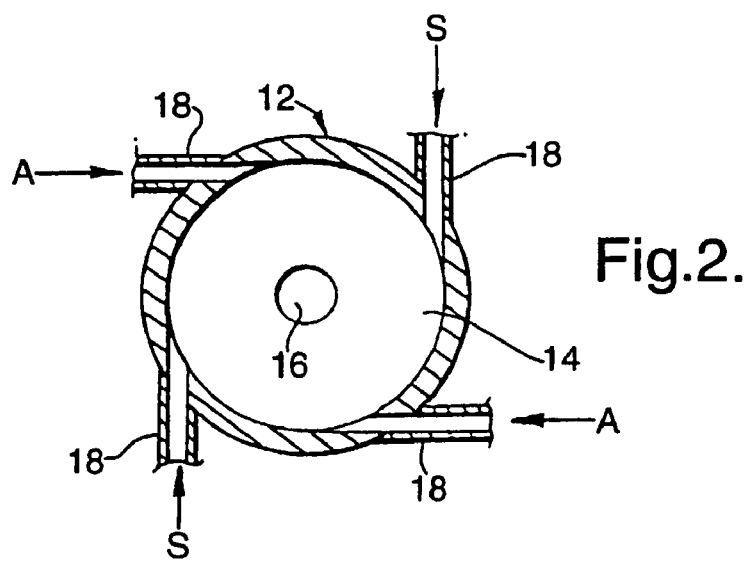
FIG. 2 shows a transverse sectional view on the line 2-2 of FIG. 1.

Referring now to FIG. 1, a crystallisation apparatus 10 comprises a vortex mixer 12 including a cylindrical chamber 14 of diameter 15 mm with an axial outlet 16 at the centre of an end wall, and with four tangential inlets 18 (only two of which are shown in FIG. 1) around its periphery. A saturated solution S of a desired substance is supplied to two inlets 18, and an anti-solvent A is supplied to the alternate two inlets, as indicated in FIG. 2. An ultrasonic probe 20 is mounted at the centre of the other end wall and projects into the middle of the chamber 14, its other end being connected to a 300 kHz transducer 22. The outlet 16 communicates with a product receiver vessel 24, an array of 20 kHz ultrasonic transducers 26 being mounted on the outside of the wall of the vessel 24.

Thus in use of the apparatus 10, the saturated solution S is thoroughly and rapidly mixed with the anti-solvent A, the volume of the chamber 14 and the flow rates being such that the residence time in the chamber 14 is for example 10 ms. The ultrasonic energy from the probe 20 insonates the entire volume of the chamber 14 with sufficient intensity to cause nucleation, as localized cavitation occurring on a microscopic scale promotes changes in fluid temperature and pressure that induce nucleation (and also promotes formation of the most stable polymorph). By adjusting the power of the ultrasound, and the residence time in the chamber 14, the degree of nucleation can therefore be controlled. The ultrasound has the additional benefit that any crystal deposits within the chamber 14 tend to be removed from the surfaces. Within the receiver vessel 24 the crystal growth process is completed, the ultrasound from the transducers 26 breaking up any crystal agglomerations and preventing surface fouling.

It will be appreciated that the solvent in the solution S and the anti-solvent A must be selected as suitable for a particular substance. Preferably they are miscible with each other. As examples, in some cases the solvent might be acetone, and the anti-solvent be water; or the solvent might be methanol and the anti-solvent be water; or the solvent might be dimethyl formamide and the anti-solvent be water. The selection of appropriate solvent and anti-solvents must be made in accordance with the substance to be crystallised.

It will also be appreciated that the ultrasound may be transmitted into a fluidic vortex chamber in which mixing is occurring in a different way, for example an ultrasonic transducer may be coupled to the end wall of the chamber. This is particularly applicable with a vortex chamber of diameter above say 20 mm, for example with a chamber of internal diameter 50 mm. Furthermore, if the crystal growth process is slow the outlet from the vessel 24 or from the fluidic mixer 14 may be supplied to a pulsed flow reactor comprising linked vortex cells in which a pulsed flow ensures a well-defined residence time, as described in GB 2 242 376 B or as described in WO 00/29545; as in the holding vessel 24, each vortex cell in such a pulsed flow reactor may be supplied with wall-mounted transducers to suppress agglomeration and prevent fouling. Such transducers may be energized continuously to encourage formation of small crystals.

In the apparatus of FIG. 1 the mixture of liquids and crystals generated in the fluidic vortex mixer 12 is fed into a receiver vessel 24 in which the crystal growth process is completed. The crystals initially formed in the mixture are small, and have a narrow size distribution. Crystal ripening may occur in the receiver vessel 24, with the larger crystals growing at the expense of the smaller crystals, which re-dissolve. If crystal ripening is not desirable, it may be preferable to omit the receiver vessel 24, and proceed directly to the formation of liquid droplets in a spray dryer, as discussed below, but in many cases any such crystal ripening is advantageous.

Figure 3:
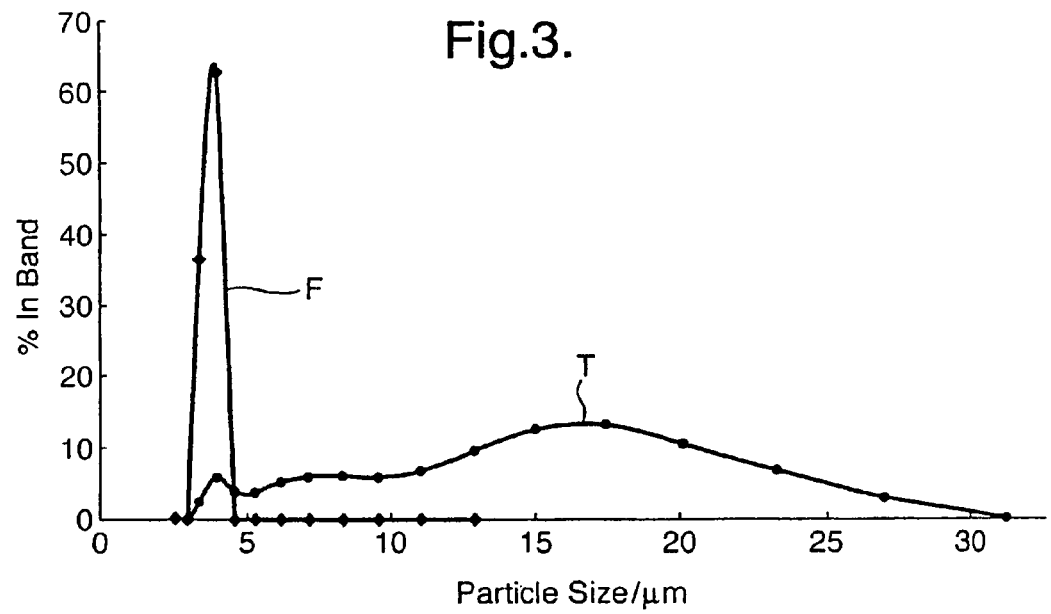
FIG. 3 shows particle size distributions for crystals made in two different ways.

Referring now to FIG. 3, the crystal size distribution (marked F) is shown for crystals of a pharmaceutical product driven out of solution by an anti-solvent (drowning out crystallisation), using such a fluidic vortex mixer 12. For comparison, the size distribution obtained with a stirred tank reactor is also shown, marked T. In the case of the fluidic mixer, crystals were trapped onto a filter paper using a vacuum pump from the spray emerging from the vortex mixer 12, to provide a sample. It will be observed that the fluidic vortex mixer gives a very narrow size distribution (about 3.0-4.5 μm), whereas the stirred tank gives a far broader size spectrum (about 3 μm to 30 μm).

Figure 4A:
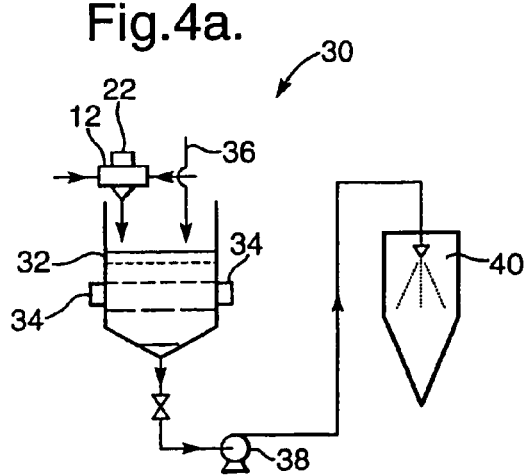
FIG. 4a shows a diagrammatic flow path of a crystal preparation apparatus incorporating the fluidic mixer of FIG. 1, in which other ingredients or diluent are added.

Referring now to FIG. 4a, a crystal preparation apparatus 30 is shown, incorporating a fluidic mixer 12 with an ultrasonic transducer 22 as shown in FIG. 1. The outlet from the fluidic mixer 12 is fed into a batch mixing tank 32 provided with ultrasonic transducers 34 coupled to the walls to suppress any agglomeration. Other ingredients are added into the tank 32 through an inlet duct 36. This could be for example an excipient, which, if it is itself crystalline, could have been produced in a second fluidic mixer 12 with an ultrasonic transducer 22 (not shown). Alternatively it might be a solution of a coating material which it is desired to absorb onto the surfaces of the crystals before they are dried. The output from the batch mixing tank 32 is pumped by a pump 38 into a spray dryer 40 which uses a pneumatic atomiser tuned to give droplet diameters not more than three times the size of the crystals. The droplets are therefore unlikely to contain more than one crystal, and will therefore dry as a single unagglomerated crystal. The output from the spray dryer 40 is therefore a free-flowing powder consisting almost exclusively of single crystals along with the coating material (or the excipient).

If the concentration of crystals in the batch mixing tank 32 is so high that there is a significant probability of two crystals being present in a droplet, the atomiser may be tuned to produce smaller droplets, or alternatively additional non-solvent liquid may be added through the duct 36 to reduce the crystal concentration.

The pneumatic atomiser is tuned by adjusting the nozzle size and/or the ratio of air to liquid fed to it. The larger the proportion of atomizing air, the smaller is the mean diameter of the droplets.

Figure 4B:
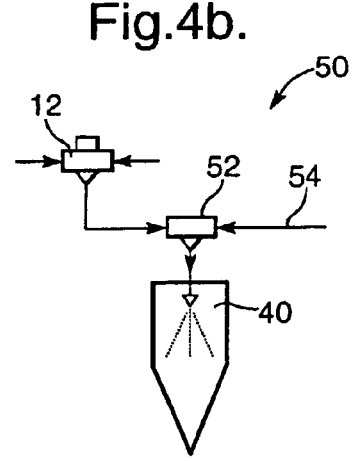

Referring now to FIG. 4b, in an alternative crystal preparation apparatus 50 the outlet from the ultrasonically irradiated fluidic mixer 12 is supplied to one inlet of a second vortex mixer 52, and the other ingredient or ingredients are supplied to another inlet of the vortex mixer 52 through a duct 54. The mixture emerging from the outlet of the second vortex mixer 52 is supplied directly (or via a pump) to a spray dryer 40. The apparatus 50 operates in substantially the same way as the apparatus 30, but can operate continuously rather than treating a batch.

Figure 5:
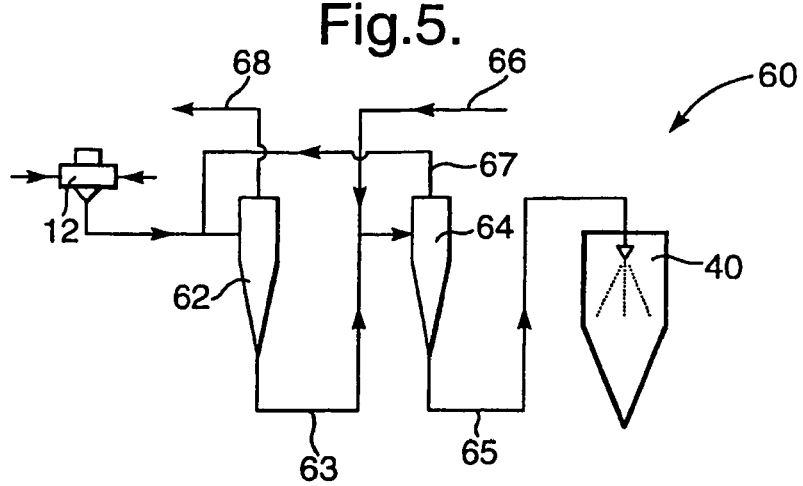
FIG. 5 shows a diagrammatic flow path of another crystal preparation apparatus incorporating the fluidic mixer of FIG. 1, in which crystals are washed before drying.

Referring now to FIG. 5, there is shown a flow diagram for a crystal preparation apparatus 60 for use in a context in which the liquid emerging from the ultrasonically irradiated fluidic mixer 12 contains solutes which are not required in the dried product. The outlet from the fluidic mixer 12 is fed into a tangential inlet of a hydrocyclone 62. The crystals emerge through the bottom of the hydrocyclone 62 (duct 63), and are fed into the tangential inlet of a second hydrocyclone 64. The crystals emerge again from the bottom (duct 65), and are then fed into the spray dryer 40. Washing liquor 66 flows through the hydrocyclones 64 and 62 in countercurrent to the crystals, the fresh liquor 66 being supplied to the tangential inlet of the second hydrocyclone 64, the liquid phase emerging from the top of the hydrocyclone 64 (duct 67) to be fed into the tangential inlet of the first hydrocyclone 62, and spent washing liquor emerges from the top of the hydrocyclone 62 (duct 68).

The hydrocyclones 62 and 64 are preferably of small diameter, for example of diameter in the range 10-25 mm, as such narrow hydrocyclones can operate with particle cut diameters less than 4 μm, for example as low as 2 μm. Suitable hydrocyclones are available from Axsia Mozley Ltd, Redruth, Cornwall. The hydrocyclones must be arranged to operate so that their particle cut size is just larger than the size of the crystals, to provide good separation between the crystals and the liquids. It will be appreciated that there might instead be a larger number of hydrocyclones in series, for example three or even four. In each case fresh washing liquor must be supplied to an inlet of the last hydrocyclone in the series, and spent washing liquor be removed from the top outlet of the first hydrocyclone.

Figure 6A:
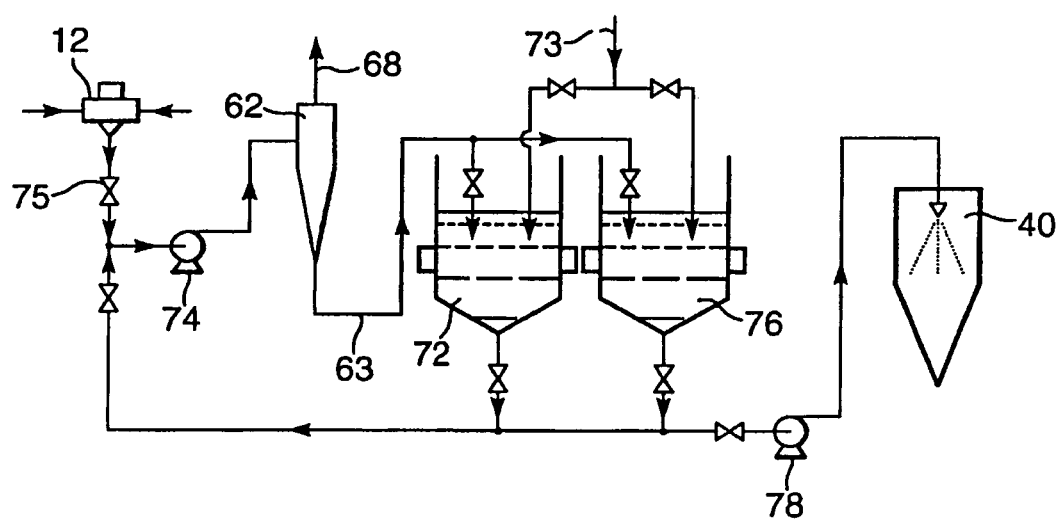
FIGS. 6a and 6b show alternatives to the apparatus of FIG. 5.

Referring now to FIG. 6a there is shown an alternative crystal preparation apparatus 70 is shown in which the liquid emerging from the fluidic mixer 12 again contains solutes which are to be removed before further processing of the crystals. In this case the process operates in a batch mode. The outlet from the fluidic mixer 12 is fed into a tangential inlet of a hydrocyclone 62. The crystals emerge from the bottom (duct 63) and are fed into a first batch mixing tank 72 to which fresh wash liquor is supplied through a duct 73; the spent washing liquor emerges from the top of the hydrocyclone 62 (duct 68). In operation the mixing tank 72 may initially be full of fresh wash liquor, and in the first stage the crystals gradually flow into the first mixing tank 72, as spent washing liquor emerges from duct 68 (to drain). As a second stage, flow through the fluidic mixer 12 is stopped (valve 75), and instead the suspension in the first mixing tank 72 is pumped by a pump 74 through the hydrocyclone 62 into a second mixing tank 76 containing fresh washing liquor. Thus during the second stage the suspension of crystals gradually flows into the second mixing tank 76, and spent washing liquor emerges from duct 68. As a third stage, the suspension of crystals may be pumped through the hydrocyclone 62 back to the first mixing tank 72, after first refilling the tank 72 with fresh wash liquor. Stages two and three can be repeated as many times as are necessary to achieve the desired degree of washing.

When the crystals have been adequately separated from the liquid contaminants, any desired additional ingredients can be added to the suspension in whichever mixing tank 72 or 76 is appropriate. The suspension can then be pumped by pump 78 to the spray dryer 40.

Figure 6B:
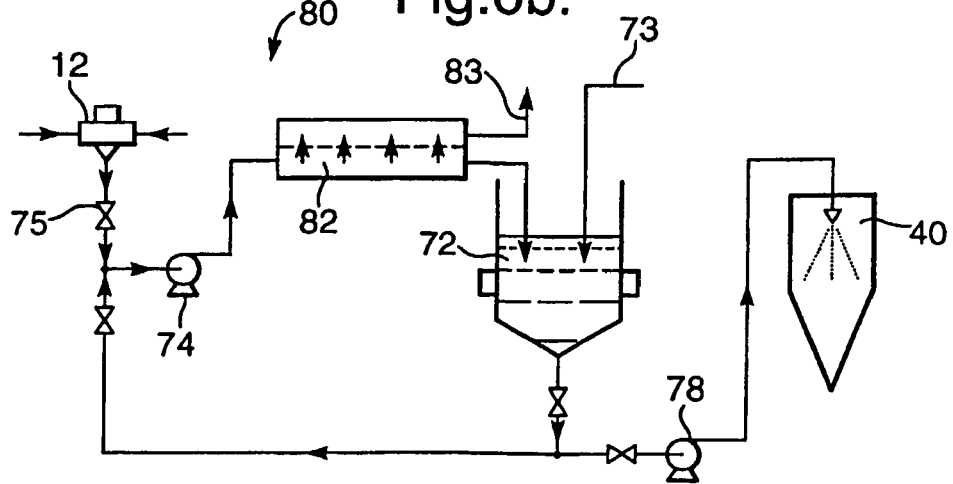

Alternatively, in place of the hydrocyclones 62 or 64, the liquid might be separated from the crystals in the washing process using a crossflow filter, either a microfilter or an ultrafilter. This is preferable where the crystals are smaller than about 2 μm, and may also be used with larger crystals. Referring to FIG. 6b, an alternative crystal preparation apparatus 80 is shown in which the liquid emerging from the fluidic mixer 12 again contains solutes which are to be removed before further processing of the crystals. In this case the process operates in a batch mode. The outlet from the fluidic mixer 12 is fed by a pump 7, through a crossflow microfilter 82. The suspension of crystals emerging from the microfilter 82 is fed into a batch mixing tank 72 to which fresh wash liquor is supplied through a duct 73; the spent washing liquor emerges as the filtrate liquid through duct 83. In operation the mixing tank 72 may initially be full of fresh wash liquor, and in the first stage the crystals gradually flow into the first mixing tank 72, as spent washing liquor emerges from duct 83 (to drain).

As a second stage, flow through the fluidic mixer 12 is stopped (valve 75), and instead the suspension in the mixing tank 72 is recirculated by the pump 74 through the microfilter 82 while continuously supplying fresh washing liquor into the mixing tank 72 to mainLain the liquid level constant. During this second stage the rate of supply of fresh washing liquor through the duct 73 is equal to the rate at which permeate liquid (spent washing liquor) emerges from the duct 83. This can be continued until the required degree of purity is achieved. Any desired additional ingredients can then be added to the suspension in the mixing tank 72, through the duct 73. The suspension can then be pumped by pump 78 to the spray dryer 40.

It will be appreciated that a crystal preparation apparatus may differ from those described above while remaining within the scope of the present invention. For example in the apparatus 60 of FIG. 5, the suspension of crystals emerging through the duct 65 from the second hydrocyclone 64 might first be passed into a batch mixing tank 32 (as in the apparatus 30) or through a second vortex mixer 52 (as in the apparatus 50) in order to dilute the suspension, prior to spray drying. This would reduce the chance of crystal agglomerates forming in the spray drying process. Furthermore, additional ingredients (whether as small crystals in suspension, or as a solution) may be added to the crystal suspension in such a batch mixing tank 32 or vortex mixer 52.

It will also be appreciated that where the process requires the addition of an additional ingredient in the form of small crystals, these crystals may be produced in a similar manner to those of the primary material. That is to say they may be produced by mixing a solvent and antisolvent in another ultrasonically irradiated fluidic vortex mixer 12, and if necessary they may be subjected to a washing step (e.g. using hydrocyclones 62 and 64, as in the apparatus 60) before being mixed as a suspension with the suspension of crystals of the primary material. In such a context, where the suspensions of crystals of the primary material and the additional ingredient emerging from the respective ultrasonically irradiated fluidic vortex mixers 12 both need to be subjected to a washing step, instead of operating the washing steps in parallel the outputs from the two fluidic vortex mixers 12 might first be mixed together, and then be subjected to a common washing step.

It will also be understood that a crystal preparation apparatus of the invention may be suitable for use in crystallising a wide variety of different compounds. Some materials for which such apparatus would be useful, in order to provide a narrow particle size distribution and so to help control bio-availability, are: analgesics such as codeine; anti-allergens such as sodium cromoglycate; antibiotics such as penicillin, cephalosporins, streptomycins, or sulphonamides; antihistamines; anti-inflammatories; bronchodilators; or therapeutic proteins and peptides. This list is not intended to be exhaustive, as the invention is applicable to substantially any crystallisation process. Other possible compounds would be amino-alcohols, pectins, and complex sugars. Other contexts in which the size distribution and mean size of particles and their morphology are important to the use of the material include dyes and pigments such as azo compounds, and photo-chromatic compounds, and the production of some catalyst materials.

For example potassium penicillin G may be precipitated from solution in n-butyl acetate using an alkaline antisolvent such as potassium hydroxide or potassium acetate solution. A further benefit in this case is that the intense mixing in the presence of ultrasound inhibits the creation of localized regions of high-pH, in which the base-catalysed formation of the impurity penicilloic acid may occur. The more uniform size distribution is desirable in this case, as is the suppression of fouling.

As another example, a range of different proteins may be precipitated. For example pectins can be precipitated from an aqueous solution using an ethanol anti-solvent, and possibly also adjustment of pH. Complex sugars such as glucosamine may also be precipitated. Other sugar-related compounds such d-maltose, sucrose, and d-cellobiose can be crystallised in a similar way: these compounds dissolve in hot water, but do not readily crystallise when cooled (a saturated solution at 50° C. will not form crystals even when cooled to 20° C. and left for 24 hours), but form small crystals in the presence of ultrasound.

The invention claimed is:

1. A method for preparing dry crystals from a suspension of crystals in suspension in a liquid, the crystals being of a well-defined size that is in the range 1 µm to 10 µm, the method being characterised by spray drying the suspension using an atomiser tuned to create small droplets in such a way that each droplet should contain not more than one crystal, the liquid being such that droplets that contain no crystals will evaporate completely.

2. A method as claimed in claim 1, also comprising treating the suspension so as to add or remove ingredients, or dilute the suspension, prior to the spray-drying step.

3. A method of preparing dry crystals from a saturated solution, in which the saturated solution is mixed with an anti-solvent by passage through a fluidic vortex mixer, the liquid within the fluidic vortex mixer being subjected to high intensity ultrasound to initiate crystallisation and so to form a suspension of crystals of a well-defined size that is in the range 1 μm to 10 μm, and characterised by treating the suspension so as to add or remove ingredients, or dilute the suspension, and then spray drying the suspension using an atomiser tuned to create small droplets in such a way that each droplet should contain not more than one crystal, so that the resulting dry crystals are of a narrow size distribution, and the liquid in the sprayed suspension being such that droplets that contain no crystals will evaporate completely.

4. A method as claimed in claim 1 wherein the atomiser is a pneumatic or rotary atomiser.

5. A method as. claimed in claim 1 wherein the droplets are about two or three times the crystal size.

6. A method as claimed in claim 5 wherein the droplets are more than about twice the crystal size, and wherein the method also comprises diluting the suspension before the spray drying step.

7. A method as claimed in claim 1 involving the step of mixing the suspension of crystals with other ingredients before the spray drying step, wherein the mixing is carried out in a batch mixing tank, or with a fluidic vortex mixer.

8. A method as claimed in claim 1 involving both the step of removing solutes from the suspension, and also the step of mixing the suspension of crystals with other ingredients, before the spray drying step.

9. A method as claimed in claim 1 involving the step of removing solutes from the suspension wherein the solutes are removed by causing the suspension to flow in counter current to a wash liquor through a series of two or more hydrocyclones.

10. A method as claimed in claim 1 involving the step of removing solutes from the suspension by combining the suspension with a wash liquid, and subjecting it to cross-flow filtration using a microfilter or ultrafilter to remove the excess liquid.

11. A method for preparing dry crystals from a suspension of crystals in a liquid, the crystals in suspension being of a well-defined size that is in the range 1 micron to 10 microns, the method being characterised by spray drying the suspension using an atomiser tuned to create small droplets in such a way that each droplet should contain not more than one crystal, the diameter of the droplets being about two times the size of the crystals in suspension, and the liquid in the sprayed suspension being such that droplets that contain no crystals will evaporate completely.

12. A method as claimed in claim 11 also comprising treating the suspension so as to add or remove ingredients, or dilute the suspension, prior to the spray-drying step.

13. A method for preparing dry crystals from a suspension of crystals in a liquid, the crystals in suspension being of a well-defined size that is in the range 1 micron to 10 microns, the method being characterised by spray drying the suspension using an atomiser tuned to create small droplets in such a way that each droplet should contain not more than one crystal, the diameter of the droplets being more than about twice the size of the crystals in suspension, and the method also comprises diluting the suspension before the spray drying step by adding non-solvent liquid.

14. A method as claimed in claim 1 wherein the suspension of crystals is produced by mixing a saturated solution with an anti-solvent and subjecting the mixture to high-intensity ultrasound.

15. A method as claimed in claim 11 wherein the suspension of crystals is produced by mixing a saturated solution with an anti-solvent and subjecting the mixture to high-intensity ultrasound.

16. A method as claimed in claim 13 wherein the suspension of crystals is produced by mixing a saturated solution with an anti-solvent and subjecting the mixture to high-intensity ultrasound.

* * * * *